(12) United States Patent
Pieper et al.

(10) Patent No.: US 9,126,875 B2
(45) Date of Patent: Sep. 8, 2015

(54) SORPTION PROCESS WITH ADDED DRYING SECTION

(71) Applicant: UOP LLC, Des Plaines, IL (US)

(72) Inventors: Jeffrey L. Pieper, Des Plaines, IL (US); Stephen W. Sohn, Arlington Heights, IL (US); Peter M. Bernard, Chicago, IL (US); Cynthia K. Zimmerman, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 258 days.

(21) Appl. No.: 13/929,353

(22) Filed: Jun. 27, 2013

(65) Prior Publication Data

US 2015/0005561 A1   Jan. 1, 2015

(51) Int. Cl.
*C07C 7/05*     (2006.01)
*C07C 7/00*     (2006.01)

(52) U.S. Cl.
CPC ..................................... *C07C 7/005* (2013.01)

(58) Field of Classification Search
None
See application file for complete search history.

(56) References Cited

U.S. PATENT DOCUMENTS

| | | |
|---|---|---|
| 2,631,727 A | 3/1953 | Cichelli |
| 3,068,627 A | 12/1962 | Sherwood |
| 3,106,591 A | 10/1963 | Kimberlin, Jr. et al. |
| 4,006,197 A | 2/1977 | Bieser |
| 4,184,943 A | 1/1980 | Anderson |
| 5,043,525 A | 8/1991 | Haizmann et al. |
| 6,348,637 B1 | 2/2002 | Harris |
| 6,395,951 B1 | 5/2002 | Hamm |
| 6,472,578 B1 | 10/2002 | Rice |

OTHER PUBLICATIONS

"Sorption Kinetics of Highter n-Paraffins on Zeolite Molecular Sieve 5A," Ind. Eng. Chem Res. 1987, 26, pp. 2544-2546.

*Primary Examiner* — Tam M Nguyen

(57) ABSTRACT

An adsorption process using a fractionation column including a drying section is described. The drying section dries the desorbent and removes water from the adsorption process resulting in increased capacity for the adsorbent bed.

15 Claims, 3 Drawing Sheets

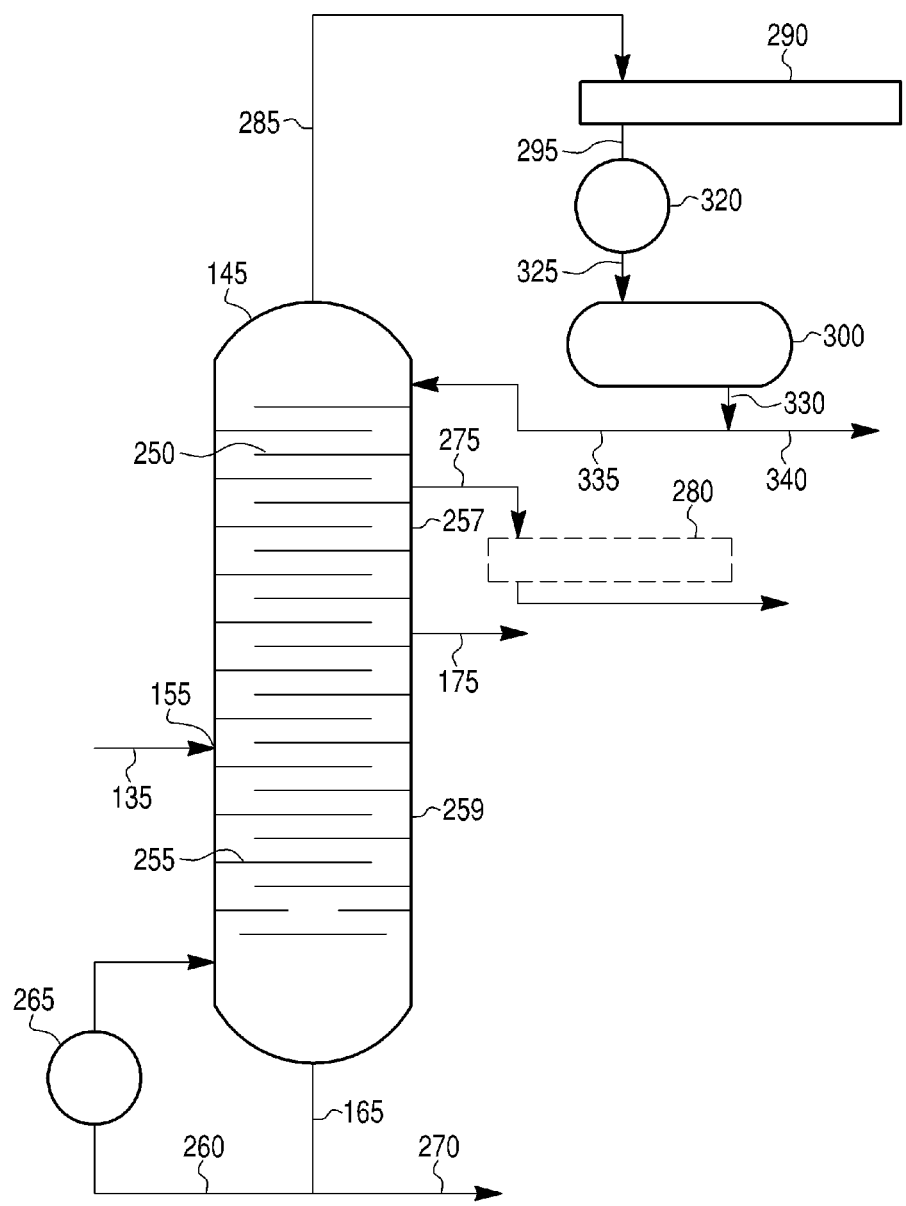

SORPTION PROCESS WITH ADDED DRYING SECTION

BACKGROUND OF THE INVENTION

The separation of various hydrocarbonaceous compounds through the use of selective adsorbents is widespread in the petroleum, chemical, and petrochemical industries. Adsorption is often utilized when it is more difficult or expensive to separate the same compounds by other means such as fractionation. Examples of the types of separations which are often performed using selective adsorbents include the separation of ethylbenzene from a mixture of xylenes, unsaturated fatty acids from saturated fatty acids, fructose from glucose, acyclic olefins from acyclic paraffins, and normal paraffins from isoparaffins. Typically, the selectively adsorbed materials have the same number of carbon atoms per molecule as the non-selectively adsorbed materials and very similar boiling points. Another common application is the recovery of a particular class of hydrocarbons from a broad boiling point range mixture of two or more classes of hydrocarbons. An example is the separation of $C_{10}$ to $C_{14}$ normal paraffins from a mixture which also contains $C_{10}$ to $C_{14}$ isoparaffins.

The success of a particular adsorptive separation is determined by many factors. Predominant among these are the composition of the adsorbent (stationary phase) and desorbent (mobile phase) employed in the process. The remaining factors are basically related to process conditions, including operating conditions, feed stream composition, and the water content of the adsorbent.

There is a need for improved adsorption processes.

SUMMARY OF THE INVENTION

One aspect of the invention is a process for the separation of a desired normal paraffin from a feed mixture comprising at least the desired normal paraffin and a non-normal paraffin. In one embodiment, the process includes passing a feed stream comprising the feed mixture through a first bed of adsorbent comprising a shape selective adsorbent and located in an adsorbent chamber which contains a plurality of compartmentalized beds of the adsorbent separated by transfer points for streams used in the process, which adsorbent selectively retains the desired normal paraffin. A desorbent stream is passed into the adsorbent chamber, an extract stream comprising the desorbent and the desired normal paraffin is withdrawn from the adsorbent chamber; and a raffinate stream comprising the desorbent and the non-normal paraffin is withdrawn from the adsorbent chamber. The transfer points in the adsorbent chamber of the feed, desorbent, extract, and raffinate streams are periodically incremented to simulate countercurrent movement of the beds of adsorbent and the feed stream. The desired normal paraffin is separated from the desorbent in an extract column having a separation section comprising a rectifying section and a stripping section, and the non-normal paraffin is separated from the desorbent in a raffinate column having a separation section comprising a rectifying section and a stripping section. The desorbent is passed through a column drying section to remove water from the desorbent, the column drying section comprising a plurality of drying trays, the column drying section positioned above the rectifying section in the raffinate column, the extract column, or both. The desired normal paraffin is then recovered.

Another aspect of the invention is an apparatus for the separation of a desired normal paraffin from a feed mixture comprising at least the desired normal paraffin and a non-normal paraffin. In one embodiment, the apparatus includes an adsorbent chamber containing a plurality of compartmentalized beds of adsorbent separated by transfer points for streams used in the process, which adsorbent selectively retains the desired normal paraffin; a rotary valve periodically incrementing the transfer points in the adsorbent chamber of feed, desorbent, extract and raffinate streams to simulate countercurrent movement of the beds of adsorbent and the feed stream; an extract column in fluid communication with the adsorbent chamber for separating the desired normal paraffin from the desorbent, the extract column having a separation section comprising a rectifying section and a stripping section; a raffinate column in fluid communication with the adsorbent chamber for separating the iso-paraffin from the desorbent, the raffinate column having a separation section comprising a rectifying section and a stripping section; a column drying section to remove water from the desorbent, the column drying section comprising a plurality of drying trays, the column drying section positioned above the rectifying section in the raffinate column, the extract column, or both.

BRIEF DESCRIPTION OF THE DRAWINGS

FIG. 3 is an illustration of another embodiment of a fractionation column according to the present invention.

DETAILED DESCRIPTION OF THE INVENTION

Figure 1:
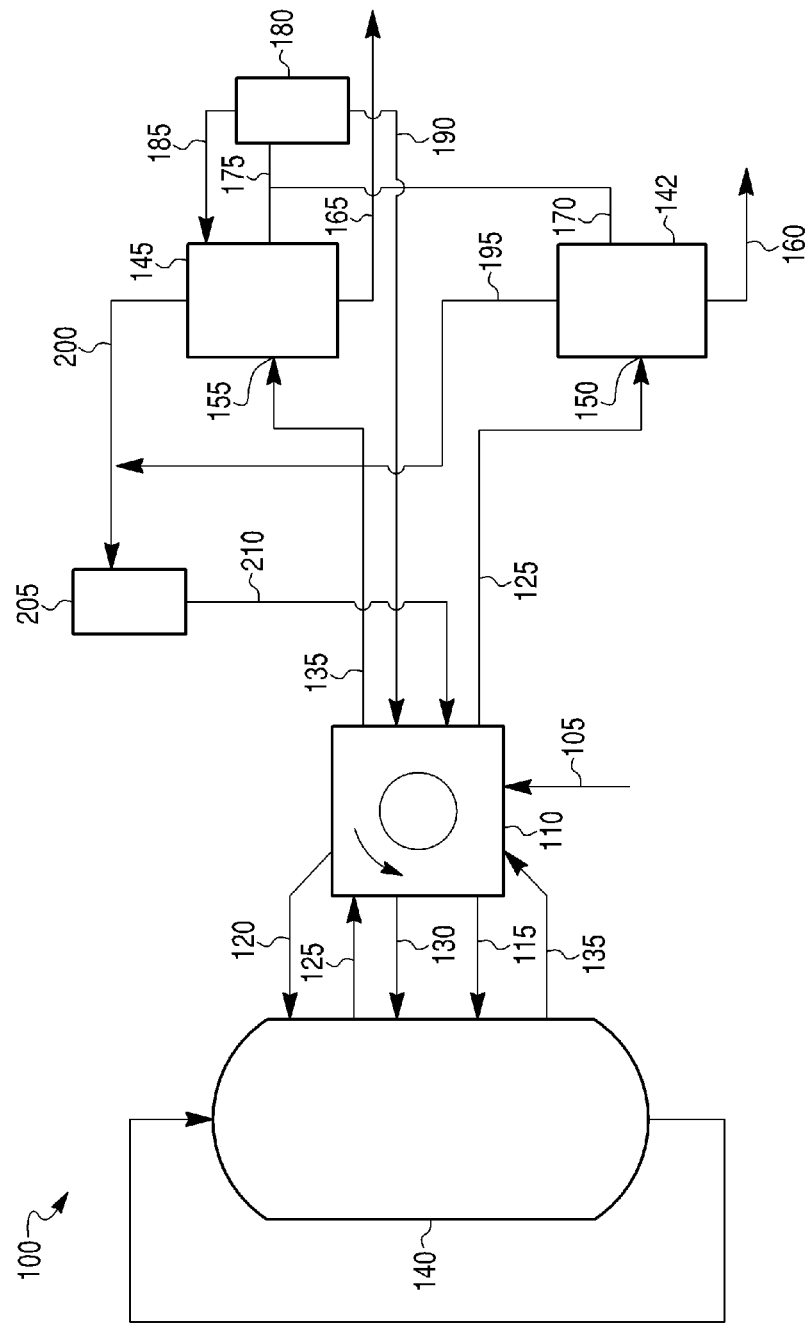
FIG. 1 is a block diagram of a typical normal paraffin adsorption unit using kerosene as a feedstock.

The adsorptive process of the present invention has cost effective design elements to manage the water content of the adsorbent and subsequent adsorbent performance in the dynamic simulated moving bed process.

Adsorptive separation processes require the sequential performance of three basic steps. The adsorbent must first be brought into contact with a feed stream comprising the particular compounds to be collected at adsorption-promoting conditions. This adsorption step should continue for a time sufficient to allow the adsorbent to collect a near equilibrium amount of the preferentially adsorbed compounds. The second basic step is the contacting of the adsorbent bearing both preferentially and non-preferentially adsorbed compounds with a material which displaces the latter from the void volume in the adsorbent bed. The second step is performed in a manner which results in the adsorbent containing significant quantities of only the preferentially absorbed feed component and the material used to displace the non-preferentially adsorbed compounds. The third basic step of the adsorptive separation process is the desorption of the preferentially adsorbed compounds. This may be performed by changing the conditions of temperature and pressure, but in the subject process, it is performed by contacting the adsorbent with a desorbent stream. The desorbent stream contains a chemical compound capable of displacing or desorbing the preferentially adsorbed compounds from the adsorbent to thereby release these compounds and prepare the adsorbent for another adsorption step.

The contacting of the adsorbent with either the feed stream or the desorbent stream leaves the interstitial void spaces between the adsorbent particles filled with the components of these particular streams. When the next contacting step begins, this residual liquid is admixed into the entering liquid. This results in the effluent streams removed from the adsorbent bed being mixtures of compounds from the two or more streams which are passed into the adsorbent bed. In the subject process, two such effluent streams are produced. They comprise a mixture of the desorbent and the preferentially adsorbed chemical compounds and a mixture of the desorbent with the chemical compounds which are not preferentially absorbed. In order to obtain a high purity product stream of the preferentially adsorbed chemical compounds and to recover the desorbent, it is necessary to fractionate these two effluent streams. The two effluent streams are therefore fractionated in two separate fractionation columns referred to as the raffinate column and the extract column.

The separation can be performed in a batch or continuous mode including the use of two or more adsorbent beds in cyclic operation. In this mode, one or more bed is used for the separation, while another bed is being regenerated. The sequential adsorption and desorption steps of an adsorptive separatory process may be performed using a fixed bed of adsorbent having fixed inlet and outlet points at opposite ends of the adsorbent bed. However, certain benefits are obtained by using a simulated moving bed of adsorbent. These benefits include the continuous production of a high purity product stream. Preferably, the countercurrent flow of the bed of solid adsorbent and the various entering liquid streams, such as the feed and desorbent streams, is simulated.

Most simulated moving bed adsorptive separation units simulate countercurrent movement of the adsorbent and the feed stream. This simulation is performed using established commercial technology wherein the adsorbent is held fixed in place as a number of sub-beds retained in one or more cylindrical adsorbent chambers. The positions at which the streams involved in the process enter and leave the chambers are slowly shifted from sub-bed to sub-bed along the length of the adsorbent chambers so that the streams enter or leave different sub-beds as the operational cycle progresses. Normally there are at least four streams (feed, desorbent, extract, and raffinate) employed in this procedure, and the location at which the feed and desorbent streams enter the chamber and the extract and raffinate streams leave the chamber are simultaneously shifted in the same direction at set intervals. Each periodic incremental shift in the location of these transfer points delivers or removes liquid from a different subbed of adsorbent within the chamber. This shifting could be performed using a dedicated line for each stream at the entrance to each sub-bed. However, this would greatly increase the cost of the process and therefore the lines are reused. Only one line is normally employed for each sub-bed, and each bed line carries one of the four process streams at some point in the cycle. This simulation procedure normally also includes the use of a variable flow rate pump which pushes liquid leaving one end of the adsorbent vessel(s) to the other end in a single continuous loop.

Simulated moving bed processes typically include at least three or four separate steps which are performed sequentially in separate zones within a mass of adsorbent retained in one or more vertical cylindrical adsorption chambers. Each of these zones normally is formed from a plurality of beds of adsorbent, sometimes referred to as sub-beds, with the number of beds per zone ranging from 2 or 3 up to 8-10. The most widely practiced commercial process units typically contain about 24 beds. All of the beds are contained in one or more vertical vessels referred to herein collectively as the adsorbent chamber. The beds are structurally separated from one another by a horizontal liquid collection/distribution grid. Each grid is connected to a transfer line defining a transfer point at which process streams such as the feed, desorbent, raffinate and extract streams enter or leave the vertical adsorption chambers.

The general technique employed in the performance of a simulated moving bed adsorptive separation is well described in the open literature. For instance a general description of a process directed to the recovery of para-xylene by simulated moving bed was presented at page 70 of the September 1970 edition of Chemical Engineering Progress (Vol. 66, No 9). A generalized description of the process with an emphasis on mathematical modeling was given at the International Conference on "Fundamentals of Adsorption", Schloss Elmau, Upper Bavaria, Germany on May 6-11, 1983 by D. B. Broughton and S. A. Gembicki. Numerous other available references describe many of the mechanical parts of a simulated moving bed system, including rotary valves for distributing various liquid flows to the bed lines, the internals of the adsorbent chambers and control systems.

Countercurrent simulated moving bed systems are described in many available references, such as U.S. Pat. No. 2,985,589, incorporated herein by reference for its teaching of the practice of simulated moving bed adsorptive separation processes. Cyclic advancement of the input and output streams of this simulation can be accomplished by a manifolding system or by rotary disc valves as shown in U.S. Pat. Nos. 3,040,777 and 3,422,848. Equipment utilizing these principles can vary in size from the pilot plant scale shown in U.S. Pat. No. 3,706,812 to commercial petrochemical plant scale, with flow rates ranging from a few cc per hour to many thousands of gallons per hour. Large scale plants normally employ rotary valves having a port for each transfer line while small scale and high pressure units tend to use valves having only two or three ports. The invention may also be practiced in a cocurrent process, like that disclosed in U.S. Pat. Nos. 4,402,832 and 4,478,721. The functions and properties of adsorbents and desorbents in the chromatographic separation of liquid components are well-known, and reference may be made to U.S. Pat. No. 4,642,397, which is incorporated herein, for additional description of these adsorption fundamentals.

It has become customary in the art to group the numerous beds in the adsorption chambers into a number of zones. Usually, the process is described in terms of 4 or 5 zones. First, contact between the feed stream and the adsorbent is made in Zone I, the adsorption zone. The adsorbent or stationary phase in Zone I becomes surrounded by liquid which contains the undesired isomer(s), that is, with raffinate. This liquid is removed from the adsorbent in Zone II, referred to as a purification zone. In the purification zone, the undesired raffinate components are flushed from the void volume of the adsorbent bed by a material which is easily separated from the desired component by fractional distillation. In the desorption zone or Zone III of the adsorbent chamber(s), the desired isomer is released from the adsorbent by exposing and flushing the adsorbent with the desorbent (mobile phase). The released desired isomer and accompanying desorbent are removed from the adsorbent in the extract stream. Zone IV is a quantity of adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. A more thorough explanation of simulated moving bed processes is given in the Adsorption, Liquid Separation section of the Kirk-Othmer Encyclopedia of Chemical Technology. The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber.

As used herein, the term "feed stream" is intended to indicate a stream in the process which comprises the feed material and which is charged to the bed of adsorbent for the purpose of recovering the extract component. The feed stream will comprise one or more extract components and one or more raffinate components. An "extract component" is a chemical compound which is preferentially adsorbed by the adsorbent which is being used as compared to a "raffinate component." Normally the term "extract component" is synonymous with the desired product of the process. For instance, normal paraffins are selectively adsorbed compared to isoparaffins and are the extract component which is recovered as a product. The other chemical compounds which were contained in the feed stream, which in some embodiments are mainly isoparaffins, become the raffinate components.

The term "extract stream" refers to a stream which contains extract components originally contained in the feed stream and which have been desorbed from the bed of adsorbent by the desorbent stream. The composition of the extract stream as it leaves the bed of adsorbent will normally vary with time and can range from a high percentage of extract components to about 100 mole percent desorbent components. The term "raffinate stream" is intended to indicate a stream originating at the bed of adsorbent and which contains the majority of the raffinate components of the feed stream. The raffinate stream is basically the unadsorbed components of the feed stream plus desorbent components which are picked up during passage through the adsorption zone. The composition of the raffinate stream as it leaves the bed of adsorbent will also vary with time from a high percentage of desorbent to a high percentage of raffinate components. Both the extract stream and the raffinate stream are normally passed into a backmixed accumulation zone (mixing drum) before being passed into the respective fractionation columns.

As used herein, the term "desorbent" is intended to indicate a chemical compound capable of desorbing the extract component from the bed of adsorbent. A "desorbent stream" is a process stream in which the desorbent is carried to the bed of adsorbent. A flush stream is also passed into the bed of adsorbent in the subject process. As used herein, the term "flush stream" is intended to refer to a stream passed into the bed of adsorbent prior to the passage of the desorbent stream into adsorbent bed for the purpose of removing substantial amounts of the raffinate components of the feed stream from the interstitial void volume and non-selective pore volume of the adsorbent bed. The flush stream will contain a "flush component" which is sometimes referred to as a sweeping agent.

The adsorbent process can be practiced using any type of commercially operable and practical selective adsorbent. The selective adsorbent can comprise a shape selective molecular sieve. The term "shape selective" refers to the molecular sieve's ability to separate molecules according to size or shape because of the fixed and relatively uniform cross-sectional diameter of the molecular sieve's pore structure. One suitable shape selective molecular sieve is a zeolite. Suitable zeolites comprise synthetic crystalline aluminosilicates. Since the pure zeolites are relatively soft and powdery, the commercially used molecular sieves comprise a binder such as clay or alumina to produce a stronger and more attrition-resistant adsorbent particle. The adsorbent particles typically have a size range of about 20 to about 40 mesh.

The particular selective adsorbent utilized in the process will depend on the hydrocarbonaceous materials which it is desired to separate. For instance, type X or type Y zeolites which contain selected cations chosen from the Group I-A and Group II-A metals may be used to separate xylene isomers. The selective adsorption of olefinic hydrocarbons from saturated hydrocarbons may be performed using a copper-exchanged Type Y zeolite as described in U.S. Pat. No. 3,720,604. The adsorbents which are preferred for the separation of normal paraffinic hydrocarbons from isoparaffinic hydrocarbons have relatively uniform pore diameters of about 5 Å such as commercially available type 5A molecular sieves produced by the UOP LLC.

Another suitable selective adsorbent comprises silicalite. Silicalite is well described in the literature. It is disclosed and claimed in U.S. Pat. No. 4,061,724 issued to Grose et al. A more detailed description is found in the article, "Silicalite, A New Hydrophobic Crystalline Silica Molecular Sieve," Nature, Vol. 271, Feb. 9, 1978 which is incorporated herein by reference for its description and characterization of silicalite. Silicalite is a hydrophobic crystalline silica molecular sieve having an MFI type structure of intersecting bent-orthogonal channels formed with two cross-sectional geometries, 6 Å circular and 5.1-5.7 Å elliptical on the major axis. This gives silicalite great selectivity as a size selective molecular sieve. Due to its aluminum free structure composed of silicon dioxide, silicalite does not show ion-exchange behavior. Thus, silicalite is not a zeolite. Silicalite is also described in U.S. Pat. Nos. 5,262,144; 5,276,246 and 5,292,900. These patents basically relate to treatments which reduce the catalytic activity of silicalite to allow its use as an adsorbent.

Although adsorptive separation processes can be operated with both vapor-phase and liquid-phase conditions, the use of liquid-phase conditions is preferred. Adsorption-promoting conditions therefore include a pressure sufficient to maintain all of the chemical compounds present in the adsorbent bed as liquids. A pressure of about 0.1 MPa (g) to about 5.0 MPa (g) may be employed, or about 0.1 MPa (g) to about 3.2 MPa. Suitable operating temperatures range from about 20° C. to about 250° C.

The feed stream includes hydrocarbon fractions having a carbon number range of from about 10 carbon atoms per molecule to about 24 carbon atoms per molecule. In some embodiments, the carbon number range of the feed stream is rather narrow and is from about 10 to 14 carbon numbers. A hydrotreated $C_{10}$ to $C_{13}$ kerosene fraction or a $C_{10}$ to $C_{20}$ gas oil fraction are representative feed streams. The feed stream may contain normal paraffins, and non-normal paraffins, but is preferably free of olefins or has a very low olefin concentration. Non-normal paraffins are typically branched paraffins and aromatics. These feed aromatics may be monocyclic aromatics such as benzene or alkylbenzenes and bicyclic aromatics including naphthalenes and biphenyls. The aromatic hydrocarbons have boiling points falling within the boiling point range of the desired extract components of the feed stream and are referred to as "co-boiling" aromatics.

The desorbent may comprise any normal paraffin or non-normal paraffin having a boiling point different from the normal paraffins in the feed stream and which is a free flowing liquid at process conditions. It can be a single component or a mixture of two or more compounds. Typically, the desorbent compound has a lower boiling point and fewer carbon atoms per molecule than the flush compound. The desorbent compound(s) typically has from about 5 to 8 carbon atoms per molecule.

The desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, the adsorbent is desirably more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or the selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in a mixture with desorbent material, and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

The flush stream is generally a raffinate-type compound which differs sufficiently in boiling point from the raffinate components of the feed stream. This allows it to be readily separated from the raffinate stream by fractionation. The flush component may be selected from the lower boiling homologs of the isoparaffins or naphthenes in the feed stream. Isooctane is a suitable flush component for use in the separation of normal paraffins from a $C_{10}$ to $C_{15}$ feed stream or a similar fraction. The isooctane is not preferentially adsorbed by the adsorbent and is easily fractionated from the $C_{10}$ to $C_{15}$ raffinate components of the raffinate stream.

Those skilled in the art will appreciate that the performance of a particular adsorbent is often greatly influenced by a number of factors not related to its composition, such as operating conditions, feed stream composition, and the water content of the adsorbent. The optimum adsorbent composition and operating conditions for the process are therefore dependent upon a number of interrelated variables. One such variable is the water content of the adsorbent, which is expressed herein in terms of the recognized Loss on Ignition (LOI) test. In the LOI test, the volatile matter content of the zeolitic adsorbent is determined by the weight difference obtained before and after drying a sample of the adsorbent at 900° C. under an inert gas purge such as nitrogen for a period of time sufficient to achieve a constant weight. The water content of the adsorbent desirably results in an LOI at 900° C. of less than 7.2% and preferably within the range of from 0 to 4.0 wt. %.

The moisture content of fresh Linde Type A (LTA) (available from UOP LLC) absorbent is typically about 5.5 wt %, with a range of about 3.8 wt % to about 7.2 wt %. It is well known that adsorbed water on LTA adsorbent suppresses the sorption rates of normal paraffins resulting in decreased capacity. Experiments have shown that there is about a 5% reduction in adsorption capacity of normal paraffins with Ca—Na LTA adsorbent in going from 3.4 wt % to 8.1 wt % water.

Another possible source of moisture in the adsorbent chambers is from make-up desorbent. The amount of make-up desorbent varies between about 1 to about 4 bbl of desorbent per 10,000 bbl of feed, depending on the degree of desorbent losses in each specific unit due to both mechanical losses and losses from the bottoms stream of the extract and raffinate fractionation columns. When using normal pentane as the desorbent, the moisture content of the make-up desorbent ranges from about 25 to about 230 wt-ppm water depending on ambient air conditions and the effectiveness of the storage tank nitrogen blanketing system.

It has been commonly accepted that the adsorbent dries down over time as fresh feed passes over the adsorbent. The moisture content of the fresh feed is less than 10 wt-ppm coming from the hydrotreater product stripper bottoms, and it ranges from about 20 to about 130 wt-ppm water depending on ambient temperatures when the fresh feed comes from unblanketed storage.

However, it was discovered in our analysis of adsorbent from commercial units, that, in some situations, the adsorbent can show an unexpectedly high water content following use, with an LOI of over 6 wt %.

A desorbent drier system could be used to dry the adsorbent. However, this involves significant capital investment and operating costs. Consequently, a lower cost alternative was developed.

The present invention instead utilizes a drying section in the extract fractionation column, the raffinate fractionation column, or both to remove water from the desorbent. The source of the water could be make-up desorbent, or it could be water removed from the adsorbent by the extract stream, raffinate stream, or both. The drying section can contain about 5 to about 10 drying trays in the column. In a typical application, the drying trays are sieve type trays, but they could also be valve type trays or other types of trays. Removing water from the desorbent should reduce the water content in the adsorbent from about 5.5 wt %, or in some unexpected cases over 6 wt %, down to almost nil, resulting in an increase in capacity of up to about 5%. The dried desorbent typically contains less than about 0.2 wt % water, or less than about 0.1 wt %, or less than about 0.08 wt %, or less than about 0.06 wt %, or less than about 0.05 wt %, or less than about 0.03 wt %, or less than about 0.02 wt %, or less than about 0.01 wt %. For the arrangement in FIG. 2, the amount of water in the dried desorbent will decrease as the amount of dry side draw desorbent becomes a greater percentage of the desorbent. The arrangement shown in FIG. 3 will allow greater removal of water. The increased capacity should offset the capital cost of adding a drying section to one or both of the fractionating columns.

As will be discussed below, the removal point for the desorbent will be changed from the discharge of the overhead reflux pump to a new side draw pump below the drying section.

One example of an adsorptive separation process 100 is illustrated in FIG. 1. Feed stream 105 enters a rotary valve 110 which is employed to direct the flow of the feed 115, desorbent 120, extract 125, flush 130, and raffinate 135 streams through a plurality of bed lines which extend from the rotary valve 110 to the adsorbent chamber 140. A commercial simulated moving bed process unit may have from 8 to 24 or more such bed lines between the rotary valve 110 and a corresponding number of adsorbent beds in one or two adsorbent chambers 140. This plurality of lines is used in the performance of the simulated moving bed separation process, which is the preferred mode of operation of the adsorption zone. However, only one set of bed lines is shown. This depiction therefore only shows the feed 115, desorbent 120, extract 125, flush 130, and raffinate 135 stream bed line flows at one particular point in time. Other bed lines are used as the locations of the adsorption zone and desorption zones are gradually shifted within the adsorbent chamber 140. The feed stream 115 enters the adsorbent chamber 140 and passes downward through a fixed mass of an adsorbent which selectively retains a hydrocarbon or class of hydrocarbons. This mass of adsorbent normally is formed from several sub-beds, each having a separate inlet line, not shown.

The liquid circulation in the adsorbent chamber 140 moves downward, and when it reaches the bottom of the chamber 140, it is pumped up to the top and moves downward through the chamber 140 again.

The extract stream 125 and raffinate stream 135 are each passed through the rotary valve 110 and sent to separate extract and raffinate fractionation columns 142, 145. The feed points 150, 155 to the extract and raffinate fractionation columns 142, 145 are separated from both extremities of the columns 142, 145 by at least four fractionation trays. The extract components of the extract stream 125 are the heaviest (highest boiling) materials fed to the extract column 142, and the raffinate components of the raffinate stream 135 are the heaviest materials fed to the raffinate column 145. The extract components of the extract stream 125 are therefore drawn off as the bottom stream 160 of the extract column 142 and may be withdrawn from the process. In a similar manner, the raffinate components of the raffinate stream 135 are removed from the process as the net bottoms stream 165 of the raffinate column 145.

The extract stream 125 and the raffinate stream 135 comprise both the desorbent compound and the flush compound. These compounds move upward through the respective columns.

In order to separate the desorbent compound and the flush compound, a liquid sidecut 170, 175 is removed from an upper intermediate point of each column 142, 145 and passed to a stripping column 180. The same stripping column 180 can be used for both as shown, or there can be separate stripping columns, if desired. The sidecut streams 170, 175 will contain an equilibrium mixture of all compounds present at the drawoff point, which is separated from the feed point 150, 155 by the number of fractionation trays required to ensure the extract and raffinate components are not present in the sidecuts 170, 175. The sidecut flow rates are operated to adjust the amount of internal reflux to ensure both the extract and raffinate components are not present in the sidecuts and desorbent is not present in the bottoms. The stripping column(s) 180 is operated at conditions effective to reject essentially all of the lowest boiling hydrocarbons present in the sidecut stream 170, 175 in an overhead vapor stream 185 and to therefore produce a net bottoms stream 190 essentially free of this lowest boiling component. The net bottoms stream 190 is the flush which can be sent to the rotary valve 110 to be fed into the adsorbent chamber 140.

The overhead vapor stream 185 of the stripping column is passed to the raffinate fractionation column 145 (with separate columns, each overhead stream would be returned to the fractionation column from which the sidecut was removed). The heat content of the stripping column overhead vapor 185 is thereby utilized within the extract fractionation column and/or the raffinate extraction column. This heat is used to improve the separation performed in the upper sections of the column and is not rejected into a separate overhead condenser as in some prior art fractionation systems. This increases the efficiency of heat utilization within the overall hydrocarbon separation process.

The overhead product 195, 200 of these fractionation columns 142, 145 comprises the desorbent compound. The overhead product 195, 200 can be combined and sent to a desorbent feed drum 205, from which the desorbent 210 can be sent to the rotary valve 110.

Figure 2:
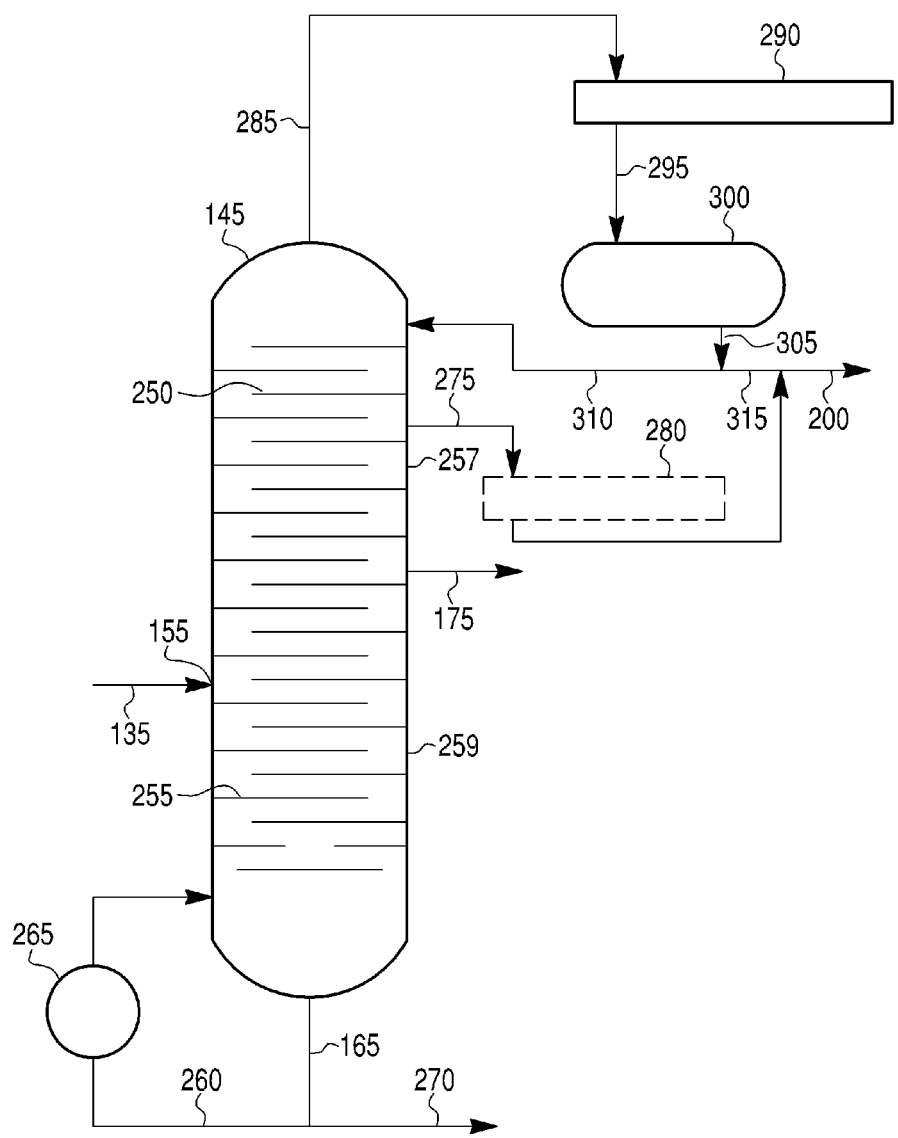
FIG. 2 is an illustration of one embodiment of a fractionation column according to the present invention.

FIGS. 2 and 3 illustrate two embodiments of the fractionation column of the present invention. The fractionation column can be the extract column 142, the raffinate column 145, or both. For ease of reference, the raffinate fractionation column will be referred to in the following discussion.

In FIG. 2, the raffinate fractionation column 145 has two sections: drying section 250 and separation section 255. Raffinate stream 135 enters the raffinate fractionation column 145 at feed point 155. The separation section 255 comprises a rectifying section 257 above the feed point 155 and a stripping section 259 below the feed point 155. Drying section 250 is above the rectifying section 257 of the separation section 255. The heavier raffinate compound flows downward and forms bottoms stream 165. A portion 260 of the bottoms stream 165 can be sent to a reboiler 265 and returned to the column 145. Another portion 270 can be sent to storage.

The reboiler 265 can use hot oil or be a fired heater. If the pressure is raised high enough in the column 145, the bottoms temperature might prevent use of hot oil, and a fired heater would be needed. When the feed contains the full carbon range of $C_{10}$ to $C_{24}$, the operating temperature would be at or above the hot oil maximum, and a fired heater might be needed.

The lighter flush and desorbent compounds flow upwards. The side cut 175 containing flush and desorbent is sent to the stripping column 180. As discussed above, the side cut withdrawal position is separated from the feed point 155 by the number of trays required to ensure that the extract and raffinate components are not present in side cut 175.

A side draw desorbent stream 275 can be removed from the column below the drying section 250 and sent to an optional desorbent side draw air cooler 280. The optional desorbent side draw air cooler 280 may be required to cool the dry side draw desorbent stream 275 to maintain the desorbent in the desorbent surge drum 205 as a single liquid phase.

The overhead vapor 285 from the column 145 is sent to a column overhead air cooler 290. The cooled overhead vapor 295 is sent to column overhead receiver 300. The saturated desorbent stream 305 from the column overhead receiver 300 can be split into two portions: reflux 310 and column net overhead 315. Water removed in the drying section 250 in excess of the saturation value of the desorbent stream 305 as determined by the pressure and temperature of the column overhead receiver 300 forms a free water phase in the column overhead receiver 300 and is collected and removed from the system by a water boot on the bottom of the column overhead receiver 300 and a water drain system (not shown). The reflux 310 is sent back to the column 145. The column net overhead 315 is combined with the dry side draw desorbent stream 275 (optionally cooled) forming a partially dry stream 200, which is sent to the desorbent surge drum 205.

As discussed, the desorbent stream 200 is a combined stream of the column net overhead 315 and the dry side draw desorbent stream 275. Without the drying section 250, the raffinate column 145 operates at overhead conditions about 0.77 kg/cm²-g and 100° C. With the drying section 250 and 50% of the desorbent stream 200 as dry side draw desorbent stream 275, the raffinate column 145 operates at overhead conditions about 1.05 kg/cm²-g and 71° C. The increase in overhead pressure and decrease in overhead temperature is a result of the desorbent and flush compounds in the overhead vapor becoming richer in desorbent as the amount of dry side draw desorbent flow increases. With 50% of the desorbent stream 200 as dry side draw desorbent stream 275 and 50% as column net overhead, the moisture in the total circulating desorbent from both the combined raffinate desorbent stream 200 and extract desorbent stream (not shown) is calculated to be reduced by about 50%, modeled using the UniSim Design software available from Honeywell.

In FIG. 3, the desorbent stream 200 is entirely taken from the dry side draw desorbent stream 275 (optionally cooled). In this case, the column pressure is raised to 1.2 kg/cm$^2$-g to help with condensing the overhead vapor 285. The overhead vapor 285 is sent to the column overhead air cooler 290. Because the air cooler alone is not sufficient, the cooled overhead vapor 295 is sent to a column overhead water cooled condenser 320. The condensed column overhead 325 is sent to column overhead receiver 300. The effluent 330 from the column overhead receiver 300 is split into a portion 335 which is refluxed to the column 145 and a light ends drag stream 340. The light ends drag stream 340 is used to remove any light materials that may enter the column as impurities with the make-up desorbent and accumulate in the overhead column, but it is normally not used. Water removed in the drying section 250 in excess of the saturation value of the desorbent stream 330 as determined by the pressure and temperature of the column overhead receiver 300 forms a free water phase in the column overhead receiver 300 and is collected and removed from the system by a water boot on the bottom of the column overhead receiver 300 and a water drain system (not shown). With all the desorbent as dry side draw desorbent stream 275, the moisture in the total circulating desorbent from both the combined dry side draw desorbent stream 275 and extract desorbent stream (not shown) is calculated to be reduced by almost 100%, modeled using the UniSim Design software available from Honeywell.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for the separation of a desired normal paraffin from a feed mixture comprising at least the desired normal paraffin and a non-normal paraffin comprising:
    passing a feed stream comprising the feed mixture through a first bed of adsorbent comprising a shape selective adsorbent and located in an adsorbent chamber which contains a plurality of compartmentalized beds of the adsorbent separated by transfer points for streams used in the process, which adsorbent selectively retains the desired normal paraffin,
    passing a desorbent stream into the adsorbent chamber;
    withdrawing an extract stream comprising the desorbent and the desired normal paraffin from the adsorbent chamber;
    withdrawing a raffinate stream comprising the desorbent and the non-normal paraffin from the adsorbent chamber;
    periodically incrementing the transfer points in the adsorbent chamber of the feed, desorbent, extract and raffinate streams to simulate countercurrent movement of the beds of adsorbent and the feed stream;
    separating the desired normal paraffin from the desorbent in an extract column having a separation section comprising a rectifying section and a stripping section;
    separating the non-normal paraffin from the desorbent in a raffinate column having a separation section comprising a rectifying section and a stripping section;
    passing the desorbent through a column drying section to remove water from the desorbent, the column drying section comprising a plurality of drying trays, the column drying section positioned above the rectifying section in the raffinate column, the extract column, or both; and
    recovering the desired normal paraffin withdrawing an overhead vapor stream comprising about 50 wt. % the desorbent from the raffinate column, the extract column, or both.

2. The process of claim 1 further comprising recycling the dried desorbent to the adsorbent chamber.

3. The process of claim 1 wherein the dried desorbent contains less than 0.2 wt % water.

4. The process of claim 1 wherein there are between 5 and 10 drying trays.

5. The process of claim 1 wherein a capacity of the adsorbent bed is increased at least about 5% compared to a process without the drying trays.

6. The process of claim 1 wherein the feed stream comprises $C_{10}$ to $C_{24}$ paraffins.

7. The process of claim 1 wherein the feed stream comprises $C_{10}$ to $C_{13}$ paraffins.

8. The process of claim 1 wherein the desorbent comprises $C_5$-$C_8$ normal paraffins, or non-normal paraffins, or combinations thereof.

9. The process of claim 1 wherein the shape selective adsorbent is a Linde Type A molecular sieve, silicalite, or combinations thereof.

10. A process for the separation of a desired normal paraffin from a feed mixture comprising at least the desired normal paraffin and a non-normal paraffin comprising:
    passing a feed stream comprising the feed mixture through a first bed of adsorbent comprising a shape selective adsorbent and located in an adsorbent chamber which contains a plurality of compartmentalized beds of the adsorbent separated by transfer points for streams used in the process, which adsorbent selectively retains the desired normal paraffin, the feed mixture comprising $C_{10}$ to $C_{24}$ paraffins;
    passing a desorbent stream comprising a $C_5$-$C_8$ normal paraffins, $C_8$ iso-paraffins, $C_8$ cycloparaffins, or combinations thereof into the adsorbent chamber;
    withdrawing an extract stream comprising the desorbent and the desired normal paraffin from the adsorbent chamber;
    withdrawing a raffinate stream comprising the desorbent and the non-normal paraffin from the adsorbent chamber;
    periodically incrementing the transfer points in the adsorbent chamber of the feed, desorbent, extract and raffinate streams to simulate countercurrent movement of the beds of adsorbent and the feed stream;
    separating the desired normal paraffin from the desorbent in an extract column having a separation section comprising a rectifying section and stripping section;
    separating the iso-paraffin from the desorbent in a raffinate column having a separation section comprising a rectifying section and stripping section;

passing the desorbent through a column drying section to remove water from the desorbent, the column drying section comprising a plurality of drying trays, the column drying section positioned above the rectifying section in the raffinate column, the extract column, or both;

recycling the dried desorbent to the adsorbent chamber; and recovering the desired normal paraffin withdrawing an overhead vapor stream comprising about 50 wt. % the desorbent from the raffinate column, the extract column, or both.

11. The process of claim 10 wherein the dried desorbent contains less than 0.2 wt % water.

12. The process of claim 10 wherein there are between 5 and 10 drying trays.

13. The process of claim 10 wherein a capacity of the adsorbent bed is increased at least about 5% compared to a process without the drying section.

14. The process of claim 10 wherein the feed stream comprises $C_{10}$ to $C_{13}$ paraffins.

15. The process of claim 10 wherein the shape selective adsorbent is Linde Type A, silicalite, or combinations thereof.

* * * * *